United States Patent
Movassaghi

(10) Patent No.: US 8,170,317 B2
(45) Date of Patent: May 1, 2012

(54) AUTOMATIC ISO-CENTERING FOR ROTATIONAL ANGIOGRAPHY

(75) Inventor: Babak Movassaghi, Denver, CO (US)

(73) Assignee: Koninklijke Philips Electronics N.V., Eindohven (NL)

( * ) Notice: Subject to any disclaimer, the term of this patent is extended or adjusted under 35 U.S.C. 154(b) by 614 days.

(21) Appl. No.: 12/375,572

(22) PCT Filed: Jul. 18, 2007

(86) PCT No.: PCT/IB2007/052855
§ 371 (c)(1),
(2), (4) Date: Jan. 29, 2009

(87) PCT Pub. No.: WO2008/015612
PCT Pub. Date: Feb. 7, 2008

(65) Prior Publication Data
US 2009/0316973 A1    Dec. 24, 2009

(30) Foreign Application Priority Data
Jul. 31, 2006    (EP) .................................... 06118154

(51) Int. Cl.
*G06K 9/00* (2006.01)

(52) U.S. Cl. ........ 382/131; 382/128; 382/130; 378/196; 378/197; 378/205

(58) Field of Classification Search .................. 382/128, 382/130, 131; 378/195–197, 205, 206
See application file for complete search history.

(56) References Cited

U.S. PATENT DOCUMENTS

| | | | |
|---|---|---|---|
| 4,339,825 A | 7/1982 | Barrett et al. | |
| 4,987,585 A | 1/1991 | Kidd et al. | |
| 6,260,999 B1 | 7/2001 | Wofford et al. | |
| 6,309,102 B1* | 10/2001 | Stenfors | 378/197 |
| 6,731,283 B1 | 5/2004 | Navab | |
| 7,744,277 B2* | 6/2010 | Noda et al. | 378/197 |
| 2002/0090058 A1 | 7/2002 | Yasuda et al. | |
| 2004/0017892 A1 | 1/2004 | Sabol et al. | |
| 2008/0118037 A1* | 5/2008 | Pescatore | 378/205 |

FOREIGN PATENT DOCUMENTS

WO    2007031945 A2    3/2007

OTHER PUBLICATIONS

S. James Chen, et al; 3-D Reconstruction of Coronary Arterial Tree to Optimize Angiographic Visualization, IEEE Transactions on Medical Imaging, vol. 19, No. 4, Apr. 2000. pp. 318-336.
R. Koppe, et al; 3D Reconstruction of Cerebral Vessel Malformations Based on Rotational Angiography (RA) Proceedings Car '97, Berlin, Jun. 25-28, 1997. pp. 145-151.
J.T. Maddux, et al; A randomized Study of the Safety and Clinical utility of Rotational Angiography Verses Standard Angiography in the Diagnosis of Coronary Artery Disease, 2004.
V. Rasche, et al; ECG-gated 3D Rotational Coronary ANgiography, in RSNA. 83$^{rd}$, Scientific Session, pp. C19-382, 2003.
B. Movassaghi, et al; A quanrtitative Analysis of 3D Coronary Modeling From Two or More Projection Images, IEEE Trans, Med. Imag., vol. 12, No. 23, 2004, pp. 1517-1531.

* cited by examiner

*Primary Examiner* — Kevin Pyo

(57) ABSTRACT

An automated and semi-automated determination of an optimal table position for rotational angiography is provided which is performed on the basis of the determination of a translation vector pointing from a point of gravity of the object of interest to an iso-center of the examination apparatus. This may reduce the amount of X-ray and contrast agent dose for the iso-centering procedure and may not depend on the user's skills.

11 Claims, 7 Drawing Sheets

(a)

(b)

AUTOMATIC ISO-CENTERING FOR ROTATIONAL ANGIOGRAPHY

The invention relates to the field of medical imaging. In particular, the invention relates to an examination apparatus for iso-centering an object of interest to be examined, a method for iso-centering an object of interest, an image processing device, a computer-readable medium and a program element.

Rotational angiography (RA) is a field of growing interest. Common applications are currently in the field of interventional neurology, as described in Koppe R, Klotz E, Op de Beek J, Aerts H, Kemkers R. 3D Reconstruction of Cerebral Vessel Malformations Based on Rotational Angiography (RA). Proceedings CAR '97, Berlin 1997.

Furthermore, there is a growing interest in the field of interventional cardiology, as described in J. T. Maddux, O. Wink, J. C. Messenger, B. M. Groves, R. Liao, J. Strzelczyk, S. Y. Chen, J. D. Carroll, "A Randomized Study of the Safety and Clinical Utility of Rotational Angiography versus Standard Angiography in the Diagnosis of Coronary Artery Disease", Catheterization and Cardiovascular Interventions, in print, 2004; V. Rasche, A. Buecker, M. Grass, R. Suurmond, R. Koppe., H. Kuehl, "ECG-gated 3D Rotational Coronary Angiography", in RSNA, 83rd Scientific Session, pp. C19-382, 2003; S. James Chen and John D. Carroll, "3D Reconstruction of Coronary Arterial Tree to Optimize Angiographic Visualization", IEEE transaction on medical imaging, Vol. 19, No. 4, April 2000; and B. Movassaghi, V. Rasche, M. Grass, M. Viergever, W. Niessen, "A quantitative analysis of 3D coronary modeling from two or more projection images", IEEE Trans. Med. Imag., vol. 12, no. 23, pp. 1517-1531, 2004.

Rotational angiography consists of a rotating X-ray, C-arm system around a region of interest, which is, for example, a contrast agent field carotid, contrast agent field coronary arteries, stents, etc, while acquiring two-dimensional X-ray angiograms. The acquired projection images can then be used for diagnostic purposes, or can be utilised to make a three-dimensional reconstruction of a region of interest.

One of the major prerequisites for applying rotational angiography is iso-centering of the object of interest. Currently this is achieved by acquiring two orthogonal series of projection images. For each series the user (for example, the physician) moves the patient table during X-ray exposure until the object is centred in both projection views. In case of coronary visualisation this procedure is commonly accompanied with contrast agent injection. Best image resolution (two-dimensional image quality and three-dimensional reconstructed image quality) is achieved when the object of interest is acquired with the smallest detector size possible.

To ensure that each acquired projection image contains the projection of the entire object, a correct iso-centering procedure has to be performed. This iso-centering procedure strongly depends on the skill and experience of the user.

It would be desirable to have an improved iso-centre determination.

According to an exemplary embodiment of the present invention, an examination apparatus for iso-centering of an object of interest to be examined is provided, the examination apparatus comprising a determination unit adapted for determining a translation vector pointing from a point of gravity of the object of interest to an iso-centre of the examination apparatus, wherein the examination apparatus is adapted for performing an iso-centering of the object of interest on the basis of the translation vector.

Therefore, according to this exemplary embodiment of the present invention, a fast and effective iso-centering may be provided yielding the optimal table position for rotational angiography. This may reduce the amount of X-ray and contrast agent dose for the iso-centering procedure and may not depend on the user's skills.

According to another exemplary embodiment of the present invention, the point of gravity is a three-dimensional point of gravity.

Therefore, three-dimensional iso-centering may be provided.

According to another exemplary embodiment of the present invention, the examination apparatus further comprises an acquisition unit adapted for performing a first short acquisition for a first acquisition geometry, resulting in first projection data. Furthermore, the acquisition unit may be adapted for performing a second short acquisition for a second acquisition geometry, resulting in second projection data.

The determination unit may further be adapted for determining the iso-centre of the examination apparatus and the point of gravity of the object of interest on the basis of the first and second projection data.

Thus, the acquisition comprises two short acquisitions, for example with the largest detector size in a fixed view mode, for two projection geometries. The two projections do not need to be orthogonal.

According to another exemplary embodiment of the present invention, the determination of the iso-centre comprises determining a three-dimensional intersection of a first line and a second line, wherein the first line points from a first focal spot to a first mid-point of a first projection image relating to the first acquisition geometry, and wherein the second line points from a second focal spot to a second mid-point of a second projection image relating to the second acquisition geometry.

This may provide for a full automated determination of the iso-centre.

According to a further exemplary embodiment of the present invention, the determination of the point of gravity of the object of interest comprises determining a first two-dimensional point of gravity of a third projection, determining a second two-dimensional point of gravity of a fourth projection, and determining a three-dimensional intersection of a third line and a fourth line. The third line points from the first focal spot to the first two-dimensional point of gravity and the fourth line points from the second focal spot to the second two-dimensional point of gravity.

This may provide for a full automated or semi-automated determination of the point of gravity of the object of interest.

According to another exemplary embodiment of the present invention, the determination unit is further adapted for transforming the translation vector into a table coordinate system, wherein the table coordinate system corresponds to degrees of freedom of a movable table unit on which the object of interest is disposed.

Furthermore, the iso-centering of the object of interest may comprise a translation of the object of interest corresponding to the translation vector.

According to another exemplary embodiment of the present invention, the determination of the first and second two-dimensional points of gravity is performed on the basis of a user interaction.

However, according to another exemplary embodiment of the present invention, the determination of the first and second two-dimensional points of gravity may be performed fully automatically on the basis of a segmentation operation.

According to another exemplary embodiment of the present invention, the examination apparatus is adapted as one of a three-dimensional computed tomography apparatus and a three-dimensional rotational X-ray apparatus.

It should be noted in this context, that the present invention is not limited to computed tomography or rotational X-ray angiography, but may always then be applied when an optimal table position for examination of an object of interest has to be determined.

According to another exemplary embodiment of the present invention, the examination apparatus is configured as one of the group consisting of a material testing apparatus and a medical application apparatus. A field of application of the invention may be medical imaging, in particular rotational angiography.

According to another exemplary embodiment of the present invention, a method for iso-centering an object of interest to be examined with an examination apparatus is provided, the method comprising the steps of determining a translation vector pointing from a point of gravity of the object of interest to an iso-centre of the examination apparatus, and performing an iso-centering of the object of interest on the basis of the translation vector.

This may provide for a fast and automated iso-centering.

Furthermore, according to another exemplary embodiment of the present invention, an image processing device for iso-centering an object of interest to be examined with an examination apparatus is provided, the image processing device comprising a memory for storing a data set of the object of interest, and a determination unit adapted for carrying out the above-mentioned method steps.

Furthermore, according to another exemplary embodiment of the present invention, a program element of iso-centering an object of interest is provided, which, when being executed by a processor, causes the processor to carry out the above-mentioned method steps.

According to another exemplary embodiment of the present invention, a computer-readable medium may be provided, in which a computer program of iso-centering an object of interest is stored which, when being executed by a processor, causes the processor to carry out the above-mentioned method steps.

It should be noted that the method for iso-centering may be embodied as the computer program, i.e. by software, or may be embodied using one or more special electronic optimisation circuits, i.e. in hardware, or the method may be embodied in hybrid form, i.e. by means of software components and hardware components.

The program element according to an exemplary embodiment of the invention is preferably loaded into working memories of a data processor. The data processor may thus be equipped to carry out embodiments of the methods of the present invention. The computer program may be written in any suitable programming language such as, for example, C++ and may be stored on a computer-readable medium, such as a CD-ROM. Also, the computer program may be available from a network, such as the World Wide Web, from which it may be downloaded into image processing units or processors, or any suitable computers.

It may be seen as the gist of an exemplary embodiment of the present invention that an automated or semi-automated determination of an optimal table position for rotational angiography is provided, the determination comprising two short acquisitions with the largest detector size in a fix view mode for two projection geometries followed by a determination of a translation vector. This may reduce the amount of X-ray and contrast agent dose for the iso-centering procedure and may not depend on the user's skills.

These and other aspects of the present invention will become apparent from and elucidated with reference to the embodiments described hereinafter.

Exemplary embodiments of the present invention will be described in the following, with reference to the following drawings.

The illustration on the drawings is schematic. In different drawings, similar or identical elements are provided with the same reference numerals.

Figure 1:
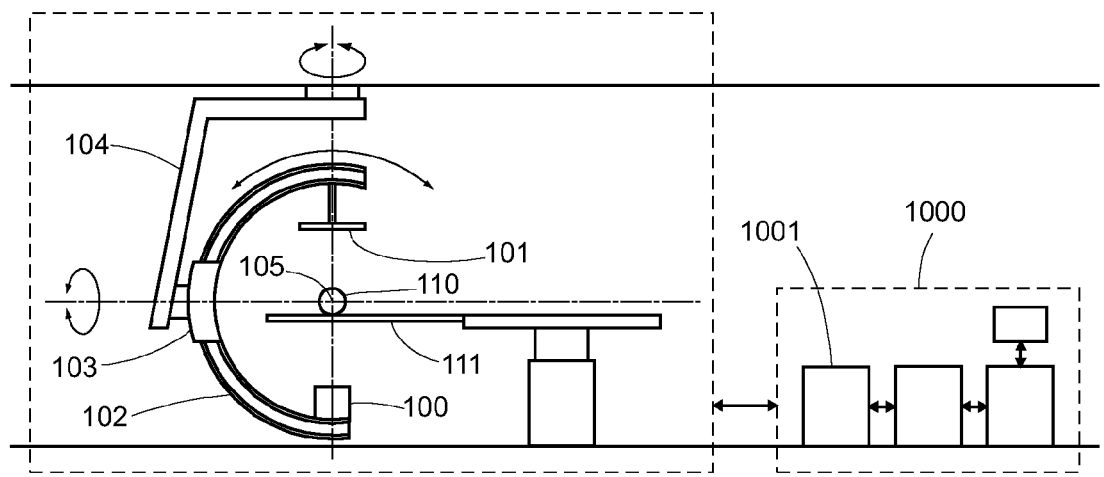
FIG. 1 shows a simplified schematic representation of a C-arm rotational X-ray examination apparatus.

FIG. 1 shows a schematic representation of an exemplary rotational X-ray scanner. An X-ray source 100 and a flat detector 101 with a large sensitive area are mounted to the ends of a C-arm 102. The C-arm 102 is held by curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are effected by servo motors. The axes of the three rotational movements and the cone-beam axis always meet in a single fixed point, the "isocenter" 105 of the rotational X-ray scanner. There is a certain volume around the isocenter that is projected by all cone beams along the source trajectory. The shape and size of this "volume of projection" (VOP) depend on the shape and size of the detector and on the source trajectory. In FIG. 1, the ball 110 indicates the biggest isocentric ball that fits into the VOP. The object (e.g. a patient or an item of baggage) to be imaged is placed on the table 111 such that the object's VOI fills the VOP. If the object is small enough, it will fit completely into the VOP; otherwise, not. The VOP therefore limits the size of the VOI.

The various rotational movements are controlled by a control unit 1001. Each triple of C-arm angle, sleeve angle, and L-arm angle defines a position of the X-ray source. By varying these angles with time, the source can be made to move along a prescribed source trajectory. The detector at the other end of the C-arm makes a corresponding movement. The source trajectory will be confined to the surface of an isocentric sphere.

Figure 2:
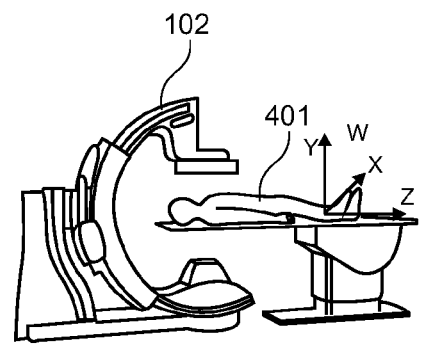
FIG. 2 shows a schematic representation of an iso-centering procedure.
Figure 2:
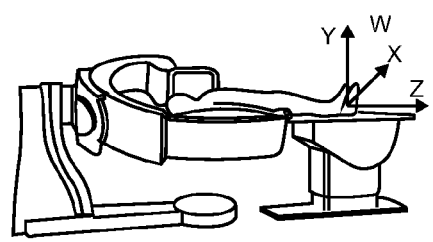

FIG. 2 shows a schematic representation of an iso-centring procedure based on two orthogonal acquired series of angiograms, which acquisition is accompanied with table movement during the X-ray exposure. The first series of angiogram data is acquired in a first position of the C-arm (see FIG. 2a). The second series of angiogram data is acquired for a second position of the C-arm of the examination apparatus, as depicted in FIG. 2b. It should be noted, that the two C-arm positions are orthogonal positions.

As described above, for each series the user moves the patient table during X-ray exposure until the object is centred in both projection views. However, determination of the optimal iso-centring strongly depends on the skill and experience of the user.

Figure 3:
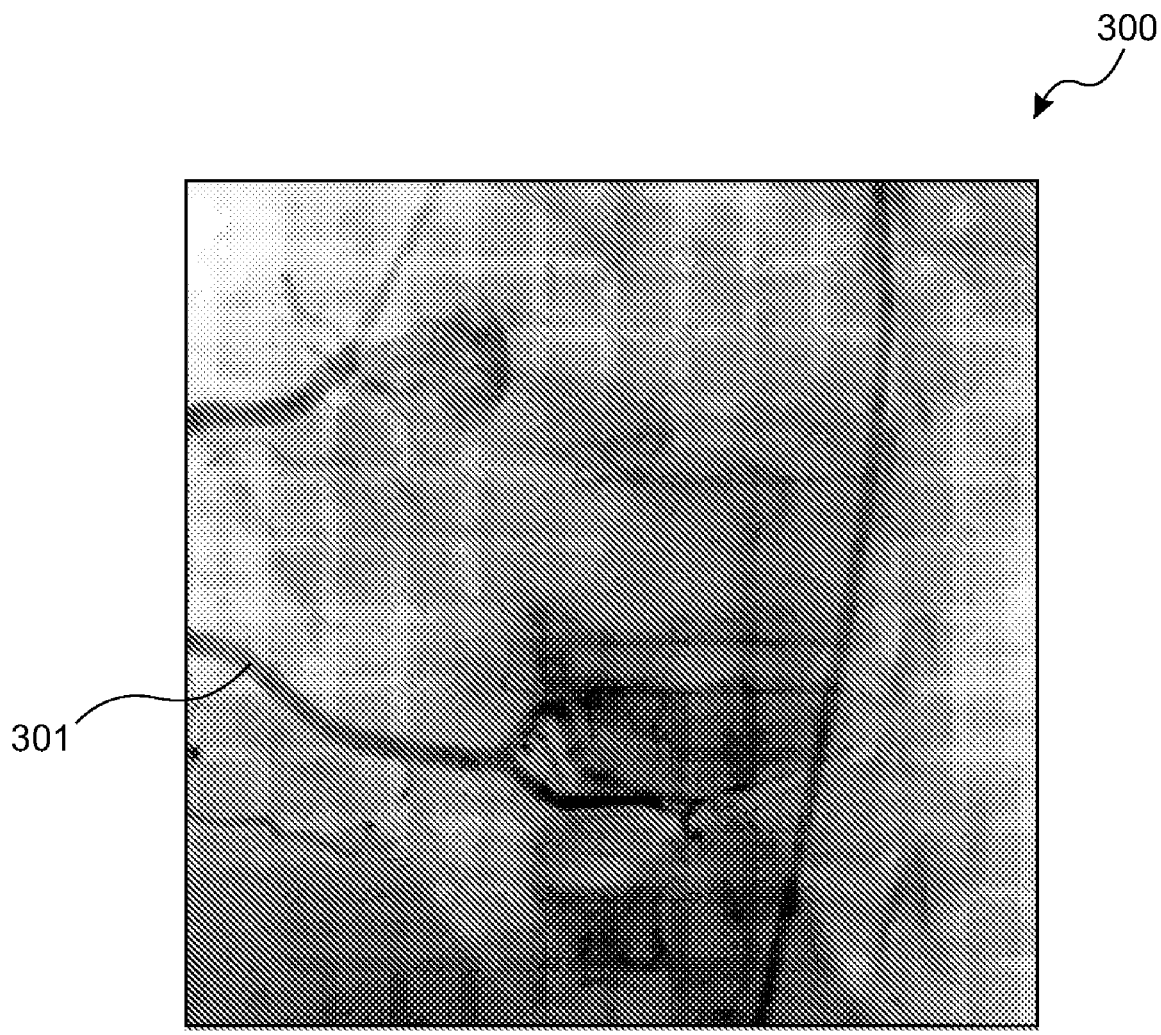
FIG. 3 shows a projection image of the right coronary artery acquired during a rotational run.

FIG. 3 shows a projection image 300 of the right coronary artery 301 acquired during a rotational run of the examination apparatus. Due to an improper pre-iso-centring procedure the object of interest (coronary artery) runs out of the picture.

According to an aspect of the present invention, an automated or semi-automated method to determine the optimal table position for rotational angiography is provided. Application of this method may reduce the amount of X-ray and contrast agent dose for the iso-centring procedure and may not depend on the physician skills.

The invention is based on two short acquisitions with the largest detector size in a fix view mode for two projection geometries.

In this context, detector size is the region of the detector that is utilized. E.g. a smaller region within the detector may be acquired where only pixels are utilized within this region. The corresponding image can then be visualized with a zoom factor.

The term fix view mode relates to an acquisition of projection images without movement of the gantry.

Figure 4:
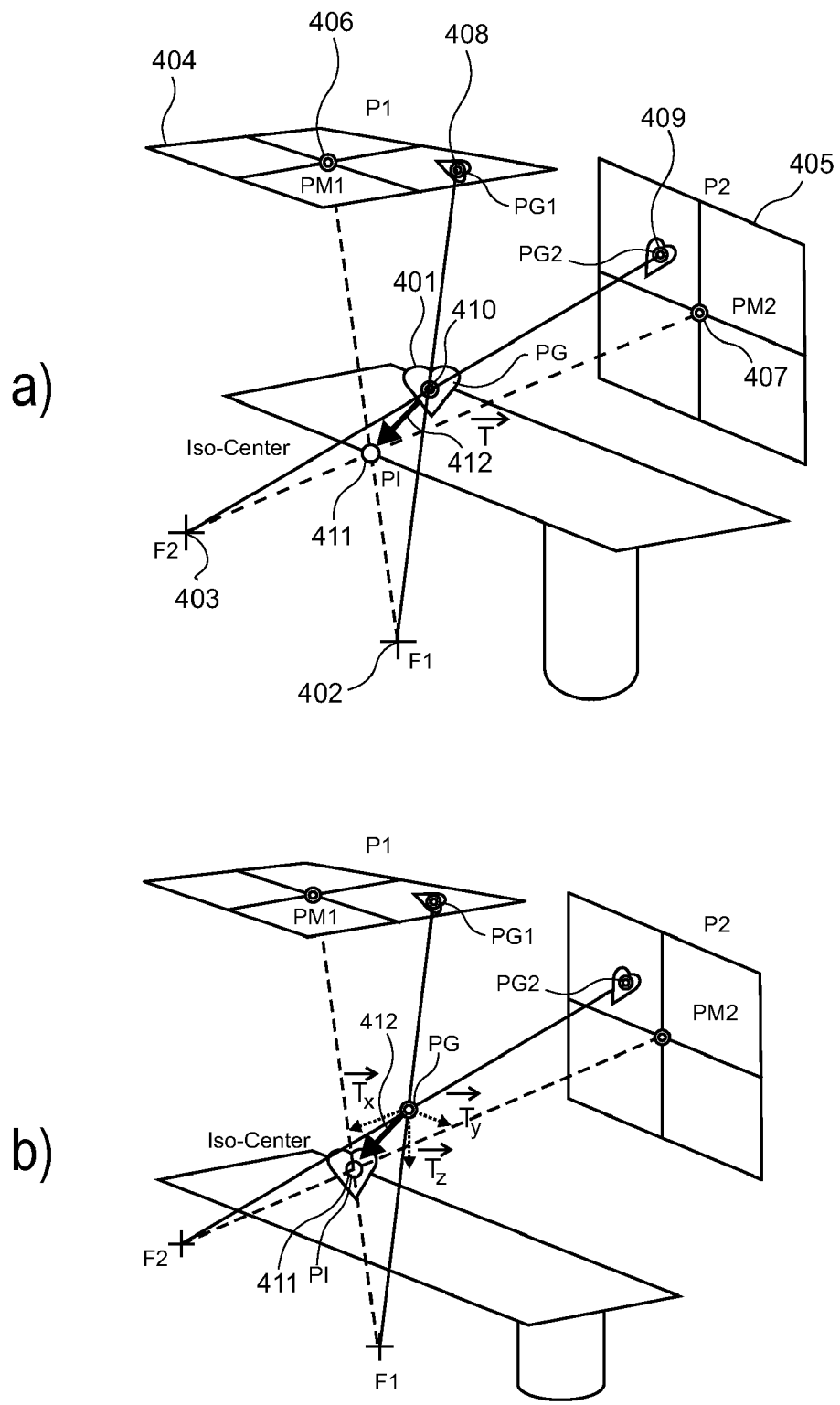
FIG. 4 shows a schematic representation of iso-centering an object of interest according to an exemplary embodiment of the present invention.

FIG. 4 shows a schematic representation illustrating the principle of an exemplary embodiment of the present invention. The object of interest is symbolised by heart 401, where $F_1$ 402 and $F_2$ 403 denote the X-ray source of the two orthogonal projection images $P_1$ and $P_2$; $P_{M1}$ and $P_{M2}$ denote the mid-points of projections $P_1$ 404 and $P_2$ 405. $P_{G1}$ 408 and $P_{G2}$ 409 denote the 2D points-of-gravity of the projected object of interest. $P_G$ 410 denotes the 3D point-of-gravity of the object of interest and $P_I$ 411 denoted the iso-center of the rotating system.

As illustrated in FIG. 4, an object of interest 401 may be iso-centred, if the translation vector 412 (T) pointing from the 3D point of gravity 410 ($P_G$) of the object of interest 401 to the iso-center of the system 411 ($P_I$) is determined. The respective vector components of T ($T_X$, $T_Y$, $T_Z$) given, for example, in the coordinate system of the table, determine then three translation components of the table movement in order to shift the $P_G$ of the object of interest to the iso-center of the system.

It should be noted that the following features may be provided in order to carry out an exemplary embodiment of the invention:

Firstly, the patient table is not moved between the two acquisitions.

Secondly, if the patient table is not programmable, measuring stripes or other means of position determination may be attached to the table to indicate a relative movement in the three axes.

Thirdly, all involved projection images may be acquired utilizing the same or subset of the projection geometry as given in the rotational acquisition protocol.

Fourthly, the geometric relation of the acquired projections must be known. This may be achieved e.g. by a pre-calibration step.

Figure 9:
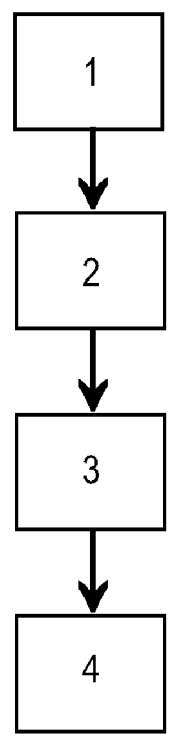
FIG. 9 shows a flow-chart of an exemplary method according to the present invention.

FIG. 9 shows a flow-chart of an exemplary embodiment of a method according to the present invention. The method depicted in FIG. 9 comprises the following steps:

Step 1: Determination of an acquisition protocol for rotational run acquisition. For example 180° propeller rotation starting from 120° LAO (left anterior oblique) to 60° RAO (right anterior oblique).

Step 2: Determination of the iso-center of the system ($P_I$) for the respective rotational run. This may be accomplished by determining the 3D intersection of the two lines pointing from the focal spots $F_1$ and $F_2$ to the mid-points $P_{M1}$ and $P_{M2}$ for the chosen projection images $P_1$ and $P_2$.

It should be noted, however, that the projection images do not need to be orthogonal.

Step 3: Determination of the 3D $P_G$ of the object of interest. For this, the point-of-gravity of the 2D projected object of interest in two chosen projections ($P_{G1}$, $P_{G2}$) must be determined. $P_G$ is calculated by the intersection of the lines pointing from the focal spot ($F_1$, $F_2$) to the respective $P_{G1}$, $P_{G2}$ (a more detailed discretion for determining $P_G$, $P_{G1}$, and $P_{G2}$ is given below).

It should be noted, that the two projections do not need to be orthogonal and do not
need to be identical as the two projections of step 2.

Step 4: Determination of the translation vector T, pointing from $P_G$ to $P_I$.

Step 5: Transformation of T into the table coordinate system (T*).

Step 6: Translation of the table according to the vector components of T* ($T^*_X$, $T^*_Y$, $T^*_Z$).

In the following the determination of the 3D point-of-gravity ($P_G$) of an object of interest is described. The calculation of $P_G$ is based on the determination of the 2D points-of-gravity ($P_{G1}$, $P_{G2}$) of the projected object of interest in two X-ray projection images.

Firstly, the $P_G$ determination is described, assuming that $P_{G1}$ and $P_{G2}$ are known. Subsequently, three possible solutions for estimating $P_{G1}$ and $P_{G2}$ are described.

It should be noted, the object of interest may also be a sub-segment of a bigger object, such as, for example, a specific vessel segment belonging to a vessel tree.

Figure 5:
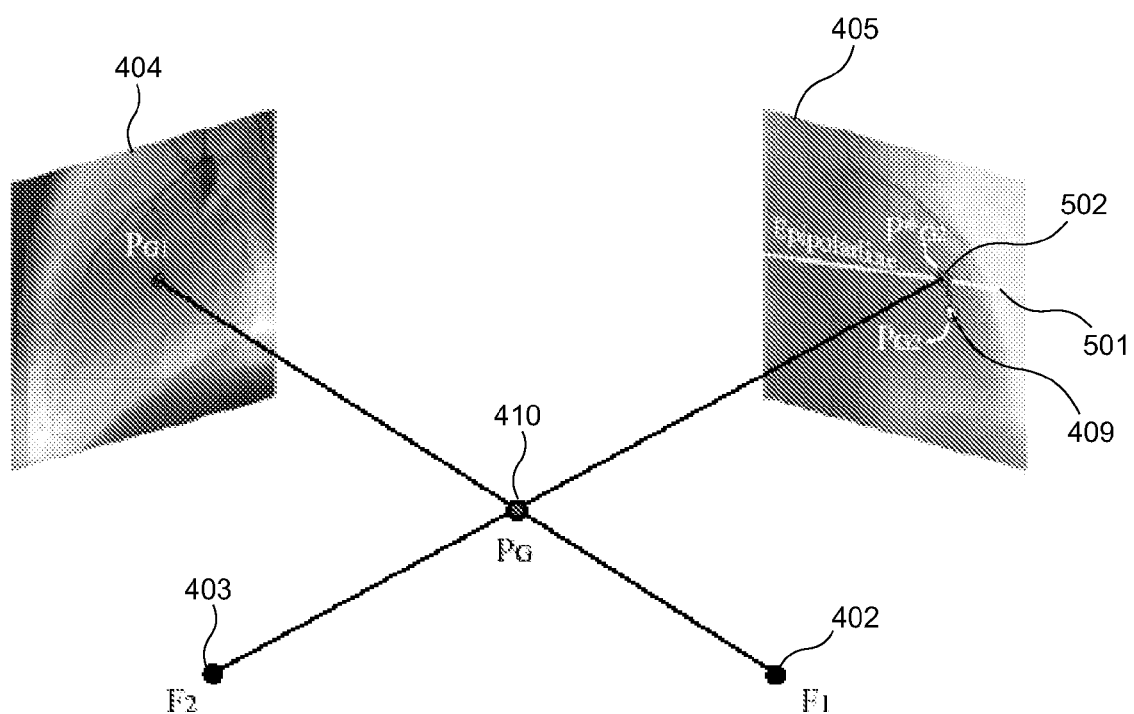
FIG. 5 shows a schematic representation of a determination of the three-dimensional point of gravity according to an exemplary embodiment of the present invention.

In the following, an exemplary $P_G$ determination scheme is described:

As illustrated in FIG. 5, for given $P_{G1}$ in a projection image $P_1$ a corresponding epipolarline (as disclosed in S. James Chen and John D. Carroll, "3D Reconstruction of Coronary Arterial Tree to Optimize Angiographic Visualization", IEEE transaction on medical imaging, Vol. 19, No. 4, April 2000, and B. Movassaghi, V. Rasche, M. Grass, M. Viergever, W. Niessen, "A quantitative analysis of 3D coronary modeling from two or more projection images", IEEE Trans. Med. Imag., vol. 12, no. 23, pp. 1517-1531, 2004) in a projection $P_2$, can be calculated.

Given the estimated $P_{G2}$ in projection $P_2$, a corresponding $P^*_{G2}$ can be determined defining the point on the epipolarline closest (Euclidian distance) to $P_{G2}$. The determination of $P^*_{G2}$ may ensure the intersection of the lines pointing from the respective X-ray sources F1 and F2 to the points $P_{G1}$ and $P^*_{G2}$.

Figure 6:
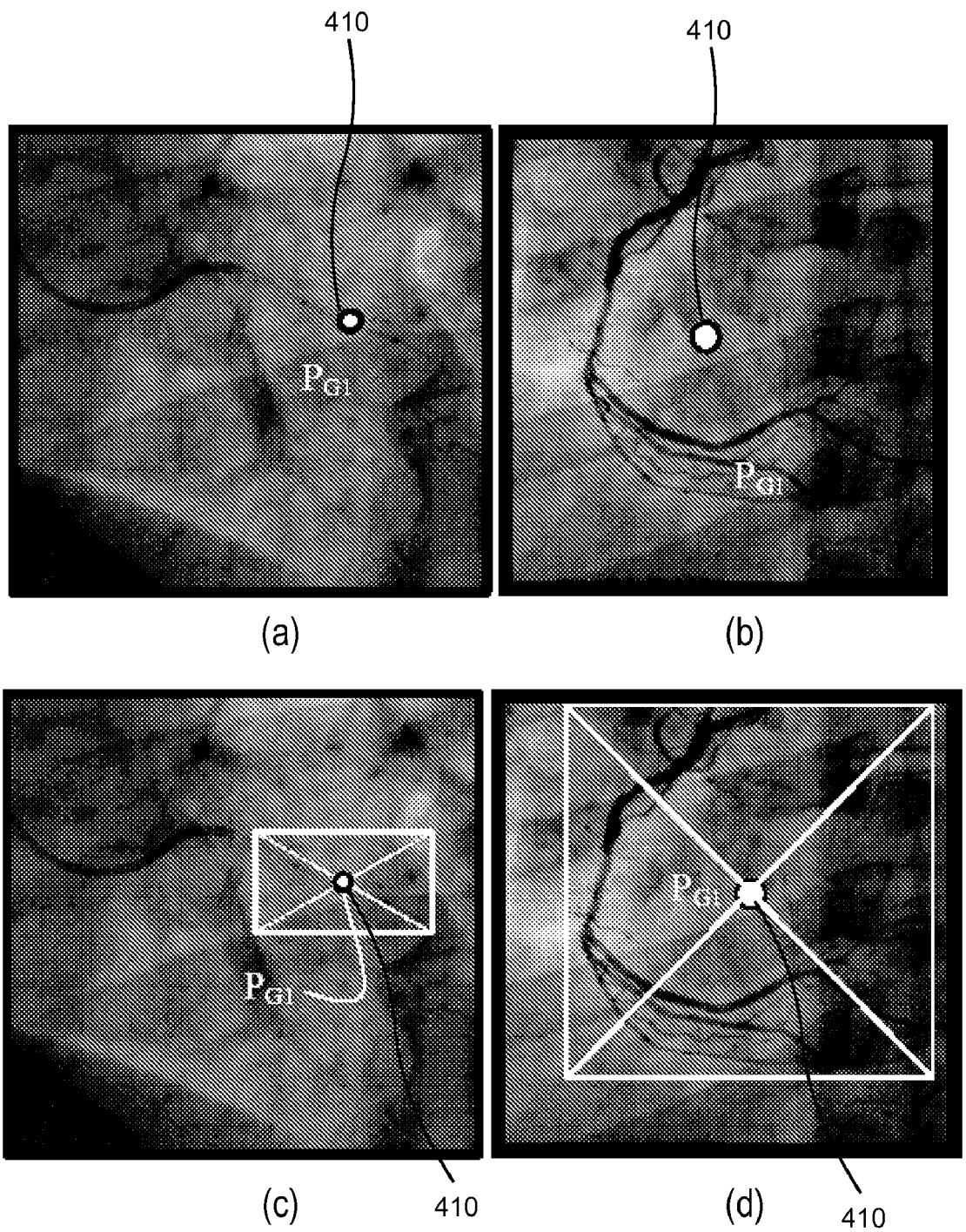
FIG. 6 shows two examples illustrating an interactive determination of a two-dimensional point of gravity according to exemplary embodiments of the present invention.

Now, three exemplary $P_{G1}$, and $P_{G2}$ determination schemes are described:

Scheme 1. Interactively by the user: For example, the user may indicate by a mouse click in each projection image the estimated point-of-gravity (as shown in FIGS. 6 (a) and (b)).

Scheme 2: Alternatively, the user determines a rectangle surrounding the object of interest in each projection from which the point-of-gravity is estimated by the intersection of the connecting lines of the corners (see FIGS. 6 (c) and (d)).

Scheme 3. Fully automatically: With the pre-knowledge of the shape of the object of interest (e.g. markers on a guide wire, coronary structures, etc.), the projected object of interest in the X-ray projection images can be segmented. The point-of-gravity can be calculated based on the pixel values belonging to the 2D object of interest in the projection images.

Figure 7:
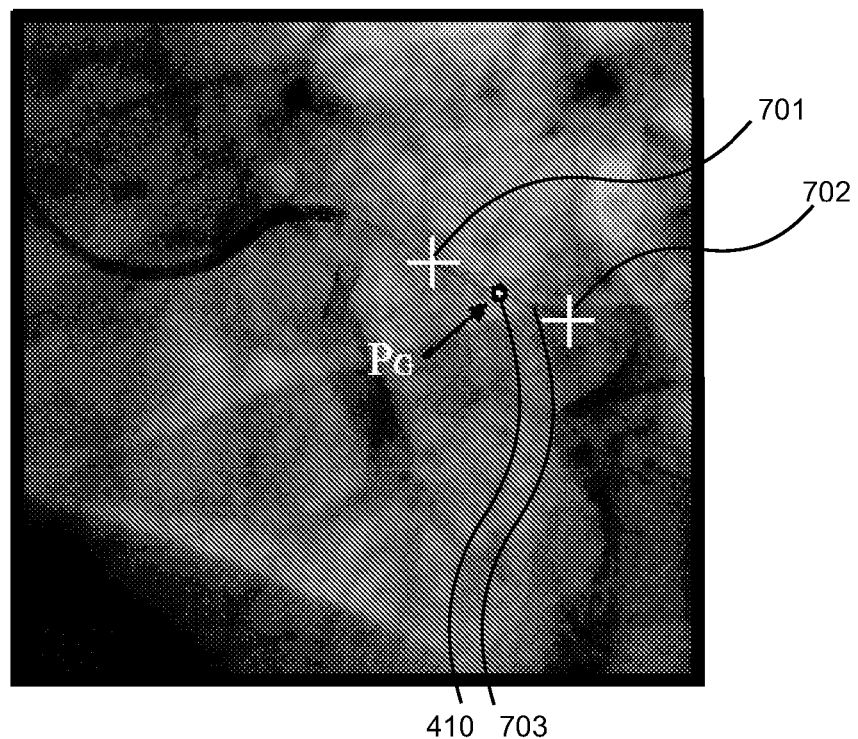
FIG. 7 shows an example illustrating the fully automatic determination of the two-dimensional point of gravity according to an exemplary embodiment of the present invention.

In FIG. 7, a first example is shown. The 2D point-of-gravity in FIG. 7 is determined based on the automatic registration of the two markers 701, 702 placed on the guide-wire 703 such as a guide-wire used in angioplasty and stenting procedures.

Figure 8:
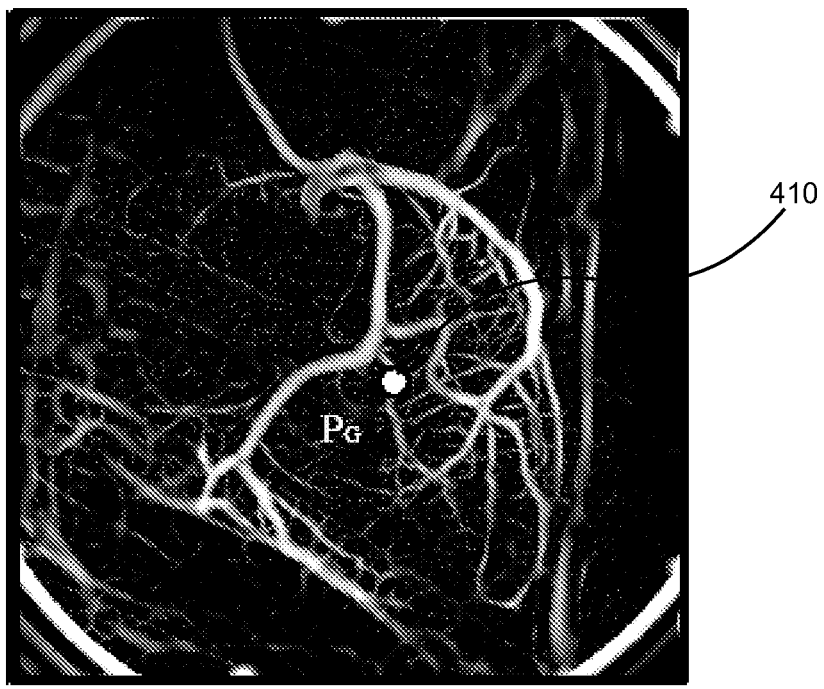
FIG. 8 shows another example illustrating the fully automatic determination of the two-dimensional point of gravity according to another exemplary embodiment of the present invention.

In FIG. 8, the point-of-gravity 410 of the left coronary tree (LCA) is estimated based on a pre filtering step where line like structures are segmented (scale space filtering).

Figure 10:
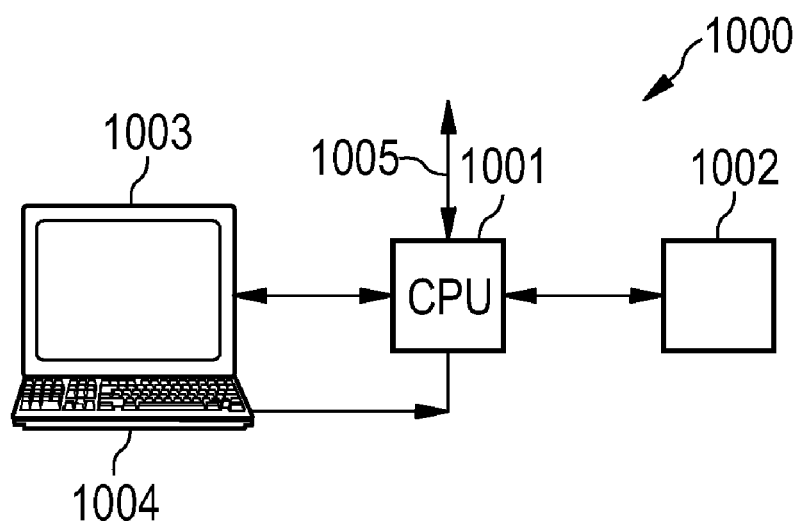
FIG. 10 shows an exemplary embodiment of an image processing device according to the present invention, for executing an exemplary embodiment of a method in accordance with the present invention.

FIG. 10 depicts an exemplary embodiment of a data processing device 1000 according to the present invention for executing an exemplary embodiment of a method in accordance with the present invention. The data processing device 1000 depicted in FIG. 10 comprises a central processing unit (CPU) or image processor 1001 connected to a memory 1002 for storing an image depicting an object of interest, such as a patient or an item of baggage. The data processor 1001 may be connected to a plurality of input/output network or diagnosis devices, such as a 3D rotational X-ray device. The data processor 1001 may furthermore be connected to a display device 1003, for example, a computer monitor, for displaying information or an image computed or adapted in the data processor 1001. An operator or user may interact with the data processor 1001 via a keyboard 1004 and/or other output devices, which are not depicted in FIG. 10.

Furthermore, via the bus system 1005, it may also be possible to connect the image processing and control processor 1001 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

The invention may be implemented for all vascular interventions where rotational acquisition is utilized.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. An examination apparatus for iso-centering an object of interest to be examined, the examination apparatus comprising:
    an X-ray acquisition unit which performs a first short acquisition for a first acquisition geometry with a focal spot in a first location, resulting in a first projection data, and which performs a second short acquisition for a second acquisition geometry with the focal spot in a second location, resulting in a second projection data;
    a data processor which determines a translation vector pointing from a point of gravity of the object of interest to an iso-centre of the examination apparatus, the data processor being programmed to:
        segment the object of interest in the first projection data;
        segment the object of interest in the second projection data;
        determine a first two-dimensional point of gravity of the segmented object of interest in the segmented first projection data automatically;
        determine a second two-dimensional point of gravity of the segmented object of interest in the segmented second projection data automatically;
        determining a first three-dimensional intersection of a first line and second line, the first line pointing from the first focal spot location to the first two-dimensional point of gravity of the segmented object of interest in the first projection data and the second line pointing from the second focal spot location to the second two-dimensional point of gravity of the segmented object of interest in the second projection data, the first three-dimensional intersection being a point of gravity of the segmented object of interest;
        determine a second three dimensional intersection of a third line and a fourth line, the third line pointing from the first focal spot location to a first mid-point of the first projection data and the fourth line pointing from the second focal spot location to a second mid-point of the second projection data, the second three-dimensional intersection being an iso-centre of the examination apparatus;
        determine a translation vector pointing from the point of gravity of the segmented object of interest to the iso-centre of the examination apparatus;
        transform the translation vector into a table coordinate system, the table coordinate system corresponding to a degrees of freedom of a movable table unit on which the object of interest is supported; and
    control the movable support unit to automatically iso-center the object of interest by shifting the movable table unit based on the translation vector.

2. The examination apparatus of claim 1, wherein the first and second acquisitions are performed in a fix view mode.

3. The examination apparatus of claim 1, wherein the determination of the first and second two-dimensional points of gravity is further refined based on a user interaction.

4. The examination apparatus of claim 1, wherein the acquisition unit includes one of a three-dimensional computed tomography apparatus and a three-dimensional rotational X-ray apparatus.

5. The examination apparatus of claim 1, configured as one of the group consisting of a material testing apparatus and a medical application apparatus.

6. A method for iso-centering an object of interest to be examined with an examination apparatus, the method comprising the steps of:
    performing a first short acquisition for a first acquisition geometry with a focal spot in a first location, resulting in a first projection image;
    performing a second short acquisition for a second acquisition geometry with the focal spot in a second location, resulting in a second projection image;
    segmenting the object of interest in the first projection image;
    segmenting the object of interest in the second projection image;

determining a first two-dimensional point of gravity in the segmented object of interest in the first projection image with a processor;

determining a second two-dimensional point of gravity in the segmented object of interest in the second projection image with the processor;

with the processor determining a first three-dimensional intersection of a first line and second line, the first line pointing from the first focal spot location to the first two-dimensional point of gravity of the segmented object of interest in the first projection image and the second line pointing from the second focal spot location to the second two-dimensional point of gravity of the segmented object of interest in the second projection image, the first three-dimensional intersection being a point of gravity of the segmented object of interest;

determining a second three dimensional intersection of a third line and a fourth line, the third line pointing from the first focal spot location to a first mid-point of the first projection image and the fourth line pointing from the second focal spot location to a second mid-point of the second projection image, the second three-dimensional intersection being an iso-centre of the examination apparatus;

determining a translation vector pointing from the point of gravity of the segmented object of interest to the iso-centre of the examination apparatus; and performing an iso-centering of the segmented object of interest on the basis of the translation vector.

7. An image processing device for iso-centering an object of interest to be examined with an examination apparatus, the image processing device comprising:

a memory for storing a data set of the object of interest;

one or more processors programmed to:

control an x-ray acquisition unit to perform a first short acquisition for a first acquisition geometry with a focal spot in a first location, resulting in a first projection image;

control the acquisition unit to perform a second short acquisition for a second acquisition geometry with the focal spot in a second location, resulting in a second projection image;

receive a plurality of user selected points adjacent a periphery of the object of interest on the first projection image;

determine a first two-dimensional point of gravity in the first projection image on the basis of a user selected plurality of points on the first projection image;

receive a plurality of user selected points adjacent a periphery of the object of interest on the second projection image;

determine a second two-dimensional point of gravity in the second projection image on the basis of the user selected plurality of points on the second projection image;

determine a first three-dimensional intersection of a first line and second line, the first line pointing from the first focal spot location to the first two-dimensional point of gravity in the first projection image and the second line pointing from the second focal spot location to the second two-dimensional point of gravity in the second projection image, the first three-dimensional intersection being the point of gravity of the object of interest;

determine a second three dimensional intersection of a third line and a fourth line, the third line pointing from the first focal spot location to a first mid-point of the first projection image and the fourth line pointing from the second focal spot location to a second mid-point of the second projection image, the second three-dimensional intersection being the iso-centre of the examination apparatus; and determine a translation vector pointing from the point of gravity of the object of interest to the iso-centre of the examination apparatus; and control iso-centering the object of interest on the basis of the translation vector.

8. A non-transitory computer-readable storage medium, in which a computer program for iso-centering an object of interest to be examined with an examination apparatus is stored which, when being executed by a processor, causes the processor to carry out the steps of:

performing a first short acquisition for a first acquisition geometry with a focal spot in a first location, resulting in a first projection image;

performing a second short acquisition for a second acquisition geometry with the focal spot in a second location, resulting in a second projection image;

segmenting the object of interest in the first projection image;

segmenting the object of interest in the second projection image;

determining a first two-dimensional point of gravity in the segmented object of interest in the first projection image with a processor;

determining a second two-dimensional point of gravity in the segmented object of interest in the second projection image with the processor;

with the processor determining a first three-dimensional intersection of a first line and second line, the first line pointing from the first focal spot location to the first two-dimensional point of gravity of the segmented object of interest in the first projection image and the second line pointing from the second focal spot location to the second two-dimensional point of gravity of the segmented object of interest in the second projection image, the first three-dimensional intersection being a point of gravity of the segmented object of interest;

determining a second three dimensional intersection of a third line and a fourth line, the third line pointing from the first focal spot location to a first mid-point of the first projection image and the fourth line pointing from the second focal spot location to a second mid-point of the second projection image, the second three-dimensional intersection being an iso-centre of the examination apparatus;

determining a translation vector pointing from the point of gravity of the segmented object of interest to the iso-centre of the examination apparatus; and performing an iso-centering of the segmented object of interest on the basis of the translation vector.

9. A non-transitory computer readable medium carrying software which controls one or more processors to perform the method of claim 6.

10. A method for iso-centering an object of interest to be examined with an examination apparatus, the method comprising the steps of:

performing a first short acquisition for a first acquisition geometry with a focal spot in a first location, resulting in a first projection data;

performing a second short acquisition for a second acquisition geometry with the focal spot in a second location, resulting in a second projection data;

determining a first two-dimensional point of gravity in the first projection data on the basis of a user selecting a plurality of points to define a boundary of a projection of the object of interest in the first projection data;

determining a second two-dimensional point of gravity in the second projection data on the basis of the user selecting a second plurality of point to define a boundary of a projection of the object of interest in the second projection data;

determining a first three-dimensional intersection of a first line and second line, the first line pointing from the first focal spot location to the first two-dimensional point of gravity of the projection of the object of interest in the first projection data and the second line pointing from the second focal spot location to the second two-dimensional point of gravity of the projection of the object of interest in the second projection data, the first three-dimensional intersection being the point of gravity of the object of interest;

determine a second three dimensional intersection of a third line and a fourth line, the third line pointing from the first focal spot location to a first mid-point of the first projection data and the fourth line pointing from the second focal spot location to a second mid-point of the second projection data, the second three-dimensional intersection being an iso-centre of the examination apparatus;

determining a translation vector pointing from the point of gravity of the object of interest to the iso-centre of the examination apparatus; and performing an iso-centering of the object of interest on the basis of the translation vector.

11. A non-transitory computer readable medium carrying software which controls one of more processors to perform the method of claim 10.

* * * * *